(12) United States Patent
Duff et al.

(10) Patent No.: US 9,913,954 B2
(45) Date of Patent: Mar. 13, 2018

(54) AUTOMATIC RISE TIME ADJUSTMENT

(75) Inventors: Winslow Kevin Duff, Export, PA (US);
Peter D. Hill, Monroeville, PA (US)

(73) Assignee: KONINKLIJKE PHILIPS N.V.,
Eindhoven (NL)

( * ) Notice: Subject to any disclaimer, the term of this patent is extended or adjusted under 35 U.S.C. 154(b) by 793 days.

(21) Appl. No.: 13/131,612

(22) PCT Filed: Nov. 21, 2009

(86) PCT No.: PCT/IB2009/055248
§ 371 (c)(1),
(2), (4) Date: May 27, 2011

(87) PCT Pub. No.: WO2010/067236
PCT Pub. Date: Jun. 17, 2010

(65) Prior Publication Data
US 2011/0226248 A1      Sep. 22, 2011

Related U.S. Application Data

(60) Provisional application No. 61/120,955, filed on Dec. 9, 2008.

(51) Int. Cl.
*A61M 16/00*      (2006.01)
*A61M 16/16*      (2006.01)

(52) U.S. Cl.
CPC .... *A61M 16/0051* (2013.01); *A61M 16/0066* (2013.01); *A61M 16/0069* (2014.02);
(Continued)

(58) Field of Classification Search
CPC .......... A61M 16/06; A61M 2016/0027; A61M 16/00; A61M 2016/0039; A61M 16/0051; A61M 16/161; A61M 16/0069; A61M 16/0066; A61M 2230/432; A61M 2230/65; A61M 2016/0021; A61M 2230/60; A61M 2205/502
(Continued)

(56) References Cited

U.S. PATENT DOCUMENTS 5,148,802 A    9/1992 Sanders
5,239,995 A    8/1993 Estes
(Continued)

FOREIGN PATENT DOCUMENTS

JP    2004526470 A    9/2004
WO    WO0226283 A2    4/2002

*Primary Examiner* — Steven Douglas
(74) *Attorney, Agent, or Firm* — Michael W. Haas

(57) ABSTRACT

A method of providing pressure support to a patient that includes determining a measure associated with an inspiratory time of the patient during therapy, delivering a flow of breathing gas to the patient at an inspiratory positive airway pressure (IPAP) level during at least a portion of an inspiratory phase of the patient, delivering the flow of breathing gas to the patient at an expiratory positive airway pressure (EPAP) level that is less than the IPAP level during at least a portion of an expiratory phase of the patient, and automatically setting a rise time associated with a transition from the EPAP level to the IPAP level based on the measure associated with the inspiratory time of the patient. Also provided is a pressure support system adapted to perform the method.

13 Claims, 8 Drawing Sheets

(52) U.S. Cl.
CPC ... *A61M 16/161* (2014.02); *A61M 2016/0021* (2013.01); *A61M 2016/0027* (2013.01); *A61M 2016/0039* (2013.01); *A61M 2205/502* (2013.01); *A61M 2230/432* (2013.01); *A61M 2230/50* (2013.01); *A61M 2230/60* (2013.01); *A61M 2230/65* (2013.01)

(58) Field of Classification Search
USPC .......................... 128/204.18, 204.21, 204.23
See application file for complete search history.

(56) References Cited

U.S. PATENT DOCUMENTS

| | | |
|---|---|---|
| 5,313,937 A | 5/1994 | Zdrojkowski |
| 5,433,193 A | 7/1995 | Sanders |
| 5,535,738 A | 7/1996 | Estes |
| 5,598,838 A | 2/1997 | Servidio |
| 5,794,615 A | 8/1998 | Estes |
| 5,865,173 A | 2/1999 | Froehlich |
| 6,105,575 A | 8/2000 | Estes |
| 6,142,150 A | 11/2000 | D'Mahoney |
| 6,305,372 B1 | 10/2001 | Servidio |
| 6,532,960 B1 | 3/2003 | Yurko |
| 6,640,806 B2 | 11/2003 | Yurko |
| 8,051,853 B2 * | 11/2011 | Berthon-Jones ......... 128/204.21 |
| 8,220,456 B2 * | 7/2012 | Kane et al. ............. 128/204.21 |
| 2003/0066528 A1 | 4/2003 | Hill |
| 2006/0070624 A1 | 4/2006 | Kane |
| 2013/0312753 A1 * | 11/2013 | Bateman ................. 128/204.23 |

* cited by examiner

AUTOMATIC RISE TIME ADJUSTMENT

CROSS-REFERENCE TO RELATED APPLICATIONS

This patent application claims the priority benefit under 35 U.S.C. § 119(e) of U.S. Provisional Application No. 61/120,955 filed on Dec. 9, 2008, the contents of which are herein incorporated by reference.

BACKGROUND OF THE INVENTION

1. Field of the Invention

The present invention generally relates to a bi-level positive airway pressure support system, and, more particularly, to a bi-level positive pressure support system and method of providing bi-level positive pressure support in which the rise time of the transition of pressure from the expiratory phase of pressure support to the inspiratory phase is automatically adjusted.

2. Description of the Related Art

Pressure support systems that provide a flow of breathing gas to an airway of a patient at an elevated pressure to treat a medical disorder are well known. One basic form of pressure support system is a continuous positive airway pressure (CPAP) system, which typically involves providing a flow of breathing gas, such as air, to a patient's airway at a constant pressure throughout a patient's breathing cycle. When used to treat obstructive sleep apnea (OSA), for example, this constant pressure is provided at a level sufficient to overcome a patient's airway resistances.

It is also known to provide a bi-level positive pressure therapy in which the pressure of gas delivered to the patient varies with the patient's breathing cycle. In a bi-level pressure support system, an inspiratory positive airway pressure (IPAP) is provided during a patient's inspiratory phase of the breathing cycle and an expiratory positive airway pressure (EPAP) is provided during the expiratory phase. The EPAP is lower than the IPAP so that the patient exhales against a relatively low pressure as compared to the IPAP pressure, thereby increasing the comfort to the patient. The BiPAP® family of pressure support devices manufactured by Philips Respironics, Inc. of Murrysville, Pa., are examples of pressure support device that provide this bi-level form of pressure support therapy. In addition, several U.S. patents describe this bi-level pressure support system in detail, including U.S. Pat. Nos. 5,433,193; 5,313,937; 5,239,995; 5,148,802; 6,532,960; and 6,640,806, the contents of all of which are hereby expressly incorporated herein by reference as if set forth in their entirety herein.

Bi-level pressure support systems as just described are often used in home settings to treat various breathing disorders, such as, without limitation, OSA. Home use of a bi-level pressure support systems currently requires a skilled provider to visit the home of the patient at least one and often several times to make sure that the system is properly set-up to provide the appropriate type of therapy to the patient. Thus, setting up and maintaining bi-level pressure support systems for home use is currently a time consuming and therefore expensive proposition. Accordingly, features that would reduce this set up time and/or minimize follow-up visits to the patient's home are valued by healthcare providers.

SUMMARY OF THE INVENTION

In one embodiment, the invention provides a method of providing pressure support to a patient that includes determining a measure associated with an inspiratory time of the patient during therapy, delivering a flow of breathing gas to the patient at an inspiratory positive airway pressure (IPAP) level during at least a portion of an inspiratory phase of the patient, delivering the flow of breathing gas to the patient at an expiratory positive airway pressure (EPAP) level that is less than the IPAP level during at least a portion of an expiratory phase of the patient, and automatically setting a rise time associated with a transition from the EPAP level to the IPAP level based on the measure associated with the inspiratory time of the patient.

In one particular embodiment, the measure associated with the inspiratory time of the patient is an average inspiratory time of the patient determined over either a predetermined number of respiratory cycles or a predetermined time period. In an alternative embodiment, the measure associated with the inspiratory time of the patient is an inspiratory time of the patient associated with a particular respiratory cycle.

The automatically setting steps may comprise multiplying the measure associated with the inspiratory time of the patient by a predetermined constant to determine the rise time. Alternatively the automatically setting comprises consulting a stored look-up table using the measure associated with the inspiratory time of the patient to determine the rise time.

In another embodiment, the method further comprises determining a measure associated with a total breath time of the patient while using the pressure support system. In this embodiment, the automatically setting step comprises automatically setting the rise time associated with the transition from the EPAP level to the IPAP level based on both the measure associated with the inspiratory time of the patient and the measure associated with a total breath time of the patient. The measure associated with the inspiratory time of the patient may be an average inspiratory time of the patient and the measure associated with a total breath time of the patient may be an average total breath time of the patient. Alternatively, the measure associated with the inspiratory time of the patient may be an inspiratory time of the patient associated with a particular respiratory cycle and the measure associated with a total breath time of the patient may be a total breath time of the patient associated with the particular respiratory cycle. In addition, the automatically setting step may, in this embodiment comprise consulting a stored look-up table using both the measure associated with the inspiratory time of the patient and the measure associated with a total breath time of the patient to determine the rise time.

In another embodiment, the invention provides a pressure support system that includes a pressure generating system adapted to produce a flow of breathing gas, a patient circuit operatively coupled to the pressure generating system to deliver the flow of breathing gas to an airway of a patient, and a controller operatively coupled to the pressure generating system. The controller is adapted to control the pressure generating system to implement the method in the various embodiments as just described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

As discussed above, a bi-level positive pressure support system provides an inspiratory positive airway pressure (IPAP) to the airway of a patient during inhalation and an expiratory positive airway pressure (EPAP) during exhalation. For most patients requiring bi-level therapy, a higher IPAP pressure is required to maintain airway patency during inhalation, and a much lower EPAP pressure is sufficient to maintain airway patency during exhalation. In fact, it is known to set the EPAP level as low as atmospheric pressure for some patients. By providing bi-level pressure support with the lowest necessary EPAP pressure, the work required for the patient to exhale is reduced and, therefore, the patient's comfort is increased. This, in turn, promotes patient compliance with the prescribed therapy.

Figure 1:
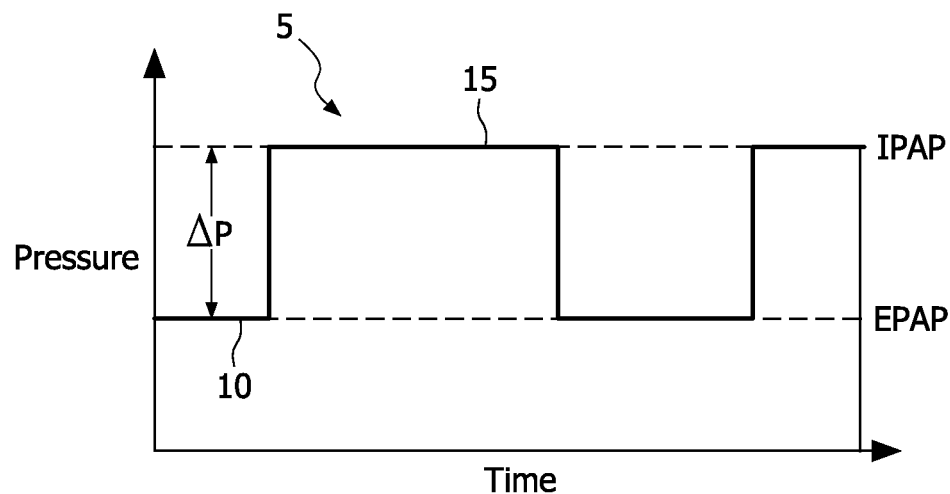
FIG. 1 is a schematic diagram showing a theoretical model pressure curve output by a bi-level positive airway pressure support system.

FIG. 1 schematically depicts a theoretical model pressure curve 5 output by a bi-level positive airway pressure support system. During an expiratory phase of the patient's breathing cycle, pressure curve 5 is at an expiratory pressure (EPAP) 10. At the end of exhalation, i.e., at the onset of the subsequent inhalation phase of the patient's breathing cycle, pressure curve 5 changes to an inspiratory pressure (IPAP) 15. When the system detects the end of inspiration, i.e., at the onset of the subsequent exhalation phase, pressure curve 5 returns to the lower expiratory pressure (EPAP) 10, and the cycle starts over. The difference in pressure between EPAP 10 and IPAP 15 is designated as ΔP in FIG. 1 and is conventionally referred to as the pressure support. In the theoretical model shown in FIG. 1, this pressure change occurs instantaneously. Thus, FIG. 1 shows the model pressure curve 5 as a square wave.

Figure 2A:
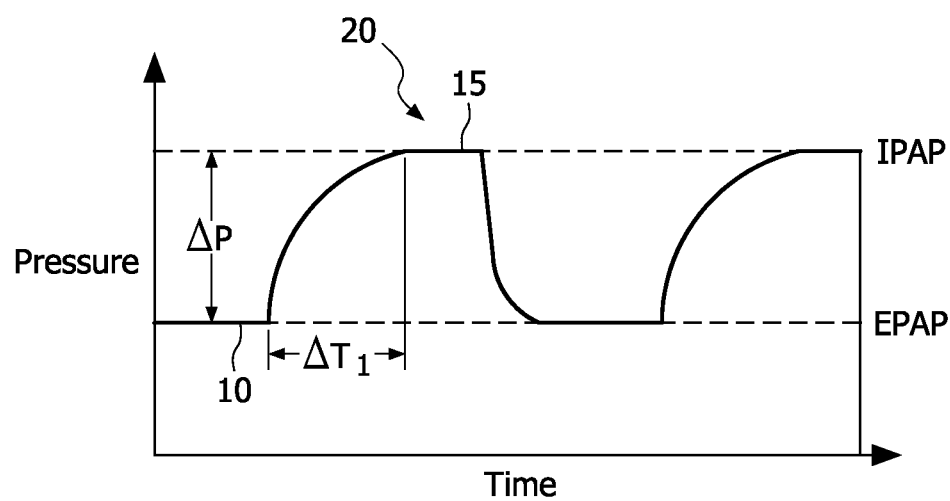
FIGS. 2A, 2B, and 2C show exemplary pressure curves having a gradual transition (to different extents) from EPAP to IPAP.
Figure 2B:
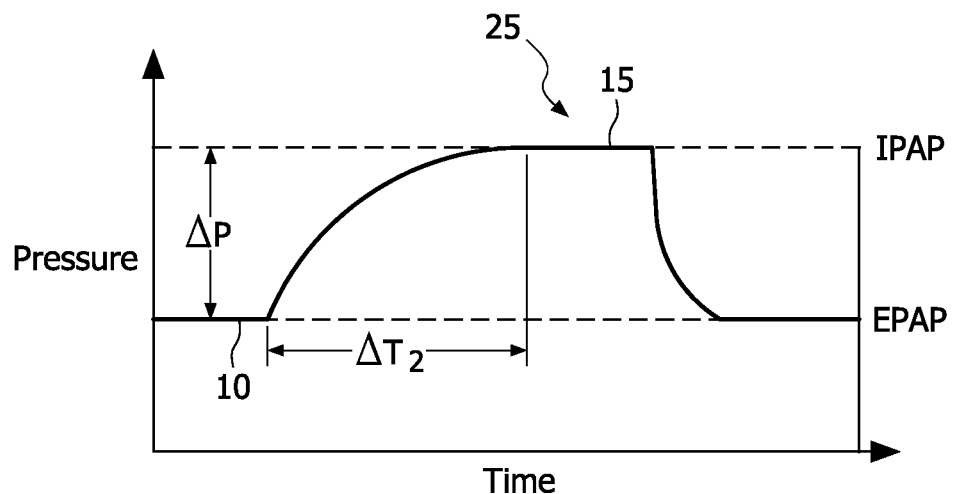
Figure 2C:
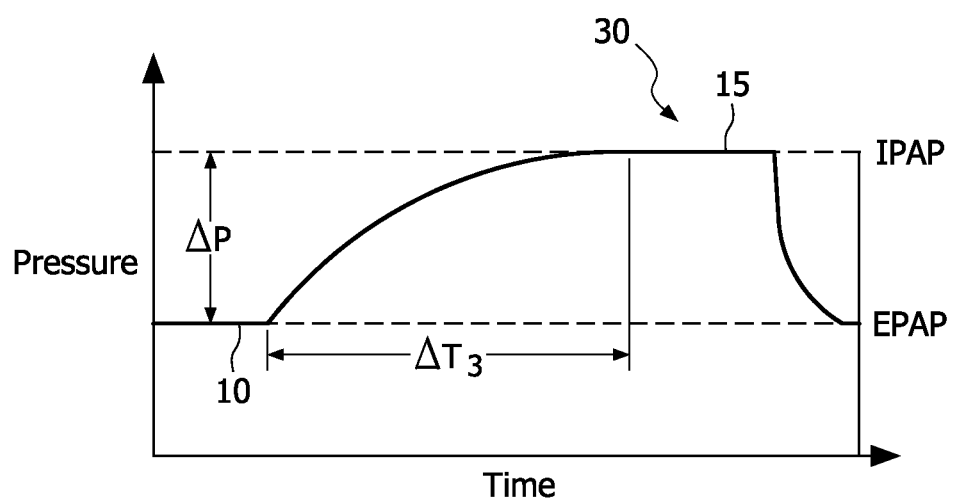

However, patient comfort may not be optimized if pressure curve 5 according to the theoretical model is applied to the patient. More specifically, rather than an instantaneous transition from EPAP to IPAP (as is the case in pressure curve 5), patient comfort may be optimized if a slightly more gradual transition is made from EPAP to IPAP and vise versa. FIGS. 2A, 2B, and 2C show such a gradual transition (to different extents) from EPAP 10 to IPAP 15 in exemplary pressure curves 20, 25, and 30. This gradual transition effect is measured by the time it takes the system pressure to increase from EPAP 10 to IPAP 15 and is referred to as the "rise time" of the bi-level pressure support system.

Similarly, rather than an instantaneous transition from IPAP 15 to EPAP 10, FIGS. 2A, 2B, and 2C show a gradual transition of the system pressure from IPAP 15 to EPAP 10. This gradual transition effect is measured by the time it takes the system pressure to decrease from IPAP 15 to EPAP 10 and is referred to as the "fall time" of the bi-level pressure support system. As described in greater detail herein and according to an embodiment of the invention, exemplary pressure curves 20, 25, and 30, or other similar pressure curves having gradual rise times, may be generated by a bi-level pressure support system 50 shown in FIG. 3.

As shown in each of FIGS. 2A, 2B, and 2C, each cycle begins with the pressure curve 20, 25, 30, as the case may be, at EPAP 10. When the pressure support system detects that the patient has finished expiration or has begun inspiration, or that some other prompting event has occurred, the system pressure is ramped up toward the level of IPAP 15. Ultimately, as seen in FIGS. 2A, 2B and 2C, the system pressure in each case reaches and levels off at the IPAP 15. Thus, the rise times in each of FIGS. 2A, 2B and 2C are shown by $\Delta T_1$, $\Delta T_2$ and $\Delta T_3$, respectively.

Furthermore, while the transition from EPAP 10 to IPAP 15 is shown as an exponential ramp in each of FIGS. 2A, 2B and 2C, that is meant to be exemplary only and it should be understood that the ramping may also be a straight line or any other transitional waveform from one generally constant level to another. For example, any monotonically increasing function may be used, such as, without limitation, sin (2*pi*t/Trt*alpha), where t is time, Trt is the rise time to 67% amplitude and alpha is the fudge factor given by arcsin(RT %)/(2*pi) (where RT % is 67% for certain products but can be generalized to a range of >0% to 100%).

In addition, while the EPAP 10 and the EPAP 15 are constant in FIGS. 2A, 2B, and 2C, it is to be understood that the EPAP 10 and the EPAP 15 need not necessarily be constant during therapy. See, for example, U.S. Pat. Nos. 5,535,738; 5,794,615; and 6,105,575, which teach varying the IPAP and/or EPAP pressure as a function of patient flow or a pre-established flow profile, the contents of each of which are incorporated herein by reference.

Moreover, in the examples shown in FIGS. 2A, 2B, and 2C, the rise time is a measure of the time for the system pressure to change from the EPAP 10 to the IPAP 15. This, however, is not meant to be limiting. For example, rather than measuring rise time from the peak-to-peak between EPAP and IPAP, the rise time can also be defined as the time it takes for the system pressure to change from a percentage, such as 10%, of its initial pressure value (e.g., EPAP) to a percentage, such as 90%, of its final pressure value (e.g., IPAP). In one particular, non-limiting embodiment, rise time is defined as the time between EPAP and K*(IPAP−EPAP) where K is typically (but not necessarily) between 50% and 90% (e.g., 67%). Thus, as used herein, the term "rise time" shall refer to a measure of the time for the system pressure to change from an initial predetermined pressure level (e.g., EPAP or some percentage thereof) to a final predetermined pressure level (e.g., IPAP, some percentage thereof or some percentage or fraction of (IPAP−EPAP)).

As seen in FIGS. 2A, 2B, and 2C, the rise time $\Delta T_1$ of pressure curve 20 is shorter than the rise time $\Delta T_2$ of pressure curve 25, which in turn is shorter than the rise time $\Delta T_3$ of pressure curve 30. It is generally believed that shorter rise times result in a decrease in comfort to the patient because of the "sharper" transient in pressure. However, shorter rise times are also believed to result in an increase in system therapeutic effectiveness. Thus, because rise time $\Delta T_2$ is shorter than rise time $\Delta T_3$, it will likely result in decreased patient comfort but increased therapy effectiveness. Rise time $\Delta T_2$, which is the shortest exemplary rise time shown, will likely result in further decreased patient comfort but further increased therapy effectiveness.

As described in greater detail herein, the present invention provides a bi-level pressure support system and method of providing bi-level pressure support in which the rise time of pressure support is automatically adjusted (to, for example, different values as illustrated in FIGS. 2A, 2B, and 2C) based on the average inspiratory time of the patient measured during a number of breathing cycles, thus eliminating the need for manual setting and adjustments of rise time parameters. In particular, a faster rise time is desirable during periods of faster breathing and a slower rise time is desirable during period of normal or calm breathing (relatively slower breathing), and thus automatically adjusting rise time as a function of inspiratory time enables optimal rise times to be employed in real time.

The present invention also contemplates that the rise time adjustment algorithm as described herein in various embodiments is implemented in a microprocessor (or similar controller)-based bi-level pressure support system. Such a system has one or more sensors, such as, for example, a flow sensor, a pressure sensor, or some other suitable sensor, which generate a one or more signals indicative of one or more characteristics associated with the flow of breathing gas provided to the patient. Furthermore, in at least one embodiment of the present invention and as described in greater detail herein, the average measured inspiratory time of the patient that is used to automatically control rise time is determined in real time by the microprocessor (or similar controller) based on the received signal or signals. The pressure support system also includes control hardware to allow the microprocessor (or similar controller) to vary the rise time as determined by the implementation of the algorithm. For example, suitable pressure support devices that can be used to implement the automatic rise time control of the present invention are the BiPAP® Duets® Bi-level System or the BiPAP® Duet® LX Bi-level System, both of which are manufactured by Philips Respironics of Murrysville, Pa. Such pressure support devices have a microprocessor, memory, pressure and flow sensors, and can be programmed in "C" or some other computer language.

Figure 3:
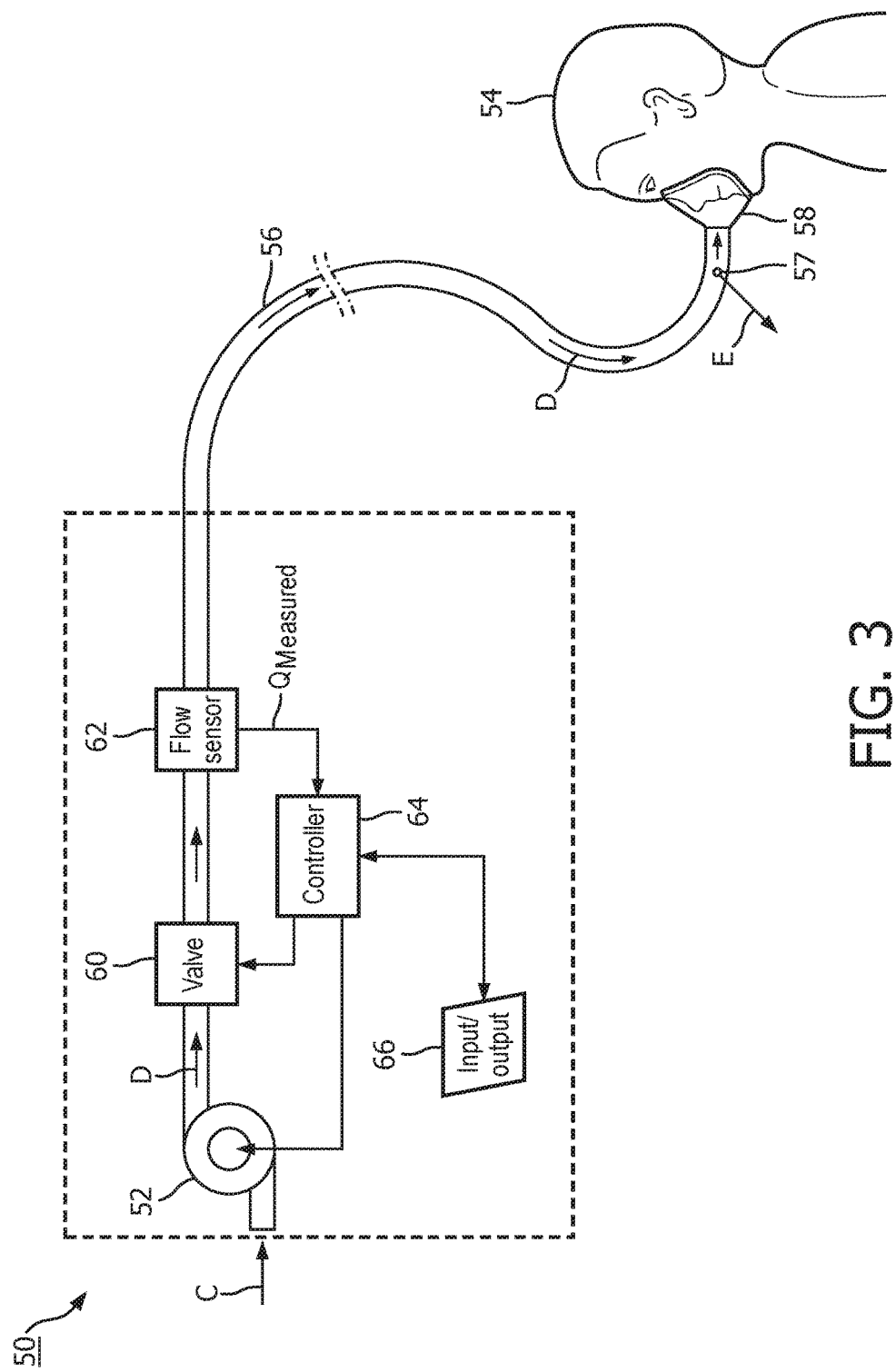
FIG. 3 is a schematic diagram of a pressure support system according to one particular, non-limiting embodiment of the invention.

FIG. 3 is a schematic diagram of a pressure support system 50 according to one particular, non-limiting embodiment of the invention which will be used herein to illustrate the present invention in its various embodiments. Referring to FIG. 3, pressure support system 50 includes a gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of a patient 54 at relatively higher and lower pressures, i.e., generally equal to or above ambient atmospheric pressure.

The pressurized flow of breathing gas, generally indicated by arrow D from gas flow generator 52, is delivered via a delivery conduit 56 to a breathing mask or patient interface 58 of any known construction, which is typically worn by or otherwise attached to a patient 54 to communicate the flow of breathing gas to the airway of the patient. Delivery conduit 56 and patient interface device 58 are typically collectively referred to as a patient circuit. In an exemplary embodiment, pressures support system 50 includes a pressure sensor operatively coupled to controller 64 for measuring the pressure of gas that is delivered to the patient. This pressure measurement can be taken either at the patient interface or closer to pressure generator 52.

The pressure support system 50 shown in FIG. 3 is what is known as a single-limb system, meaning that the patient circuit includes only a delivery conduit 56 connecting the patient 54 to the pressure support system 50. As such, an exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery conduit and an exhaust conduit connected to patient 54. In a two-limb system, the exhaust conduit carries exhaust gas from the patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment of the present invention shown in FIG. 3, patient interface 58 is a nasal mask. It is to be understood, however, that the patient interface 58 can include a nasal/oral mask, nasal pillows, tracheal tube, endotracheal tube, or any other device that provides a suitable gas flow communicating function. Also, for purposes of the present invention, the phrase "patient interface" can include the delivery conduit 56 and any other structures that connect the source of pressurized breathing gas to the patient.

In the illustrated embodiment, pressure support system 50 includes a pressure controller in the form of a valve 60 provided in delivery conduit 56. Valve 60 controls the pressure of the flow of breathing gas from flow generator 52 delivered to the patient 54. For present purposes, flow generator 52 and valve 60 are collectively referred to a pressure generating system because they act in concert to control the pressure and/or flow of gas delivered to the patient. However, it should be apparent that other techniques for controlling the pressure of the gas delivered to the patient, such as varying the blower speed of flow generator 52, either alone or in combination with a pressure control valve, are contemplated by the present invention. Thus, valve 60 is optional depending on the technique used to control the pressure of the flow of breathing gas delivered to the patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes a flow sensor 62 that measures the flow of the breathing gas within the delivery conduit 56. In the particular embodiment shown in FIG. 3, flow sensor 62 is interposed in line with delivery conduit 56, for example downstream of the valve 60. Flow sensor 62 generates a flow signal $Q_{MEASURED}$ that is provided to a controller 64 and is used by the controller 64 to determine the flow of gas at patient 54. Of course, other techniques for measuring the respiratory flow of patient 54 are contemplated by the present invention, such as, without limitation, measuring the flow directly at the patient or at other locations along delivery conduit 56, measuring patient flow based on the operation of flow generator 52, and measuring patient flow using a flow sensor upstream of valve 60.

Controller 64 may be, for example, a microprocessor, a microcontroller or some other suitable processing device, that includes or is operatively coupled to a memory (not shown) that provides a storage medium for data and software executable by controller 64 for controlling the operation of pressure support system 50, including monitoring characteristics of patient respiration and controlling the flow of breathing gas based thereon as described in greater detail herein. Finally, an input/output device 66 is provided for setting various parameters used by pressure support system 50, as well as for displaying and outputting information and data to a user, such as a clinician or caregiver.

As described in greater detail elsewhere herein, according to an aspect of the present invention in its various embodiments, data relating to patient inspiratory time is processed continuously by pressure support system 50 during operation, resulting in continuous automatic adjustment to the rise time based on the data relating to patient inspiratory time. Because the rise time is automatically adjusted, the rise time necessary for sufficient therapy may be optimized from patient to patient, from night to night, and even from minute to minute on a particular patient and does not require any intervention of the patient or caregiver.

Figure 4:
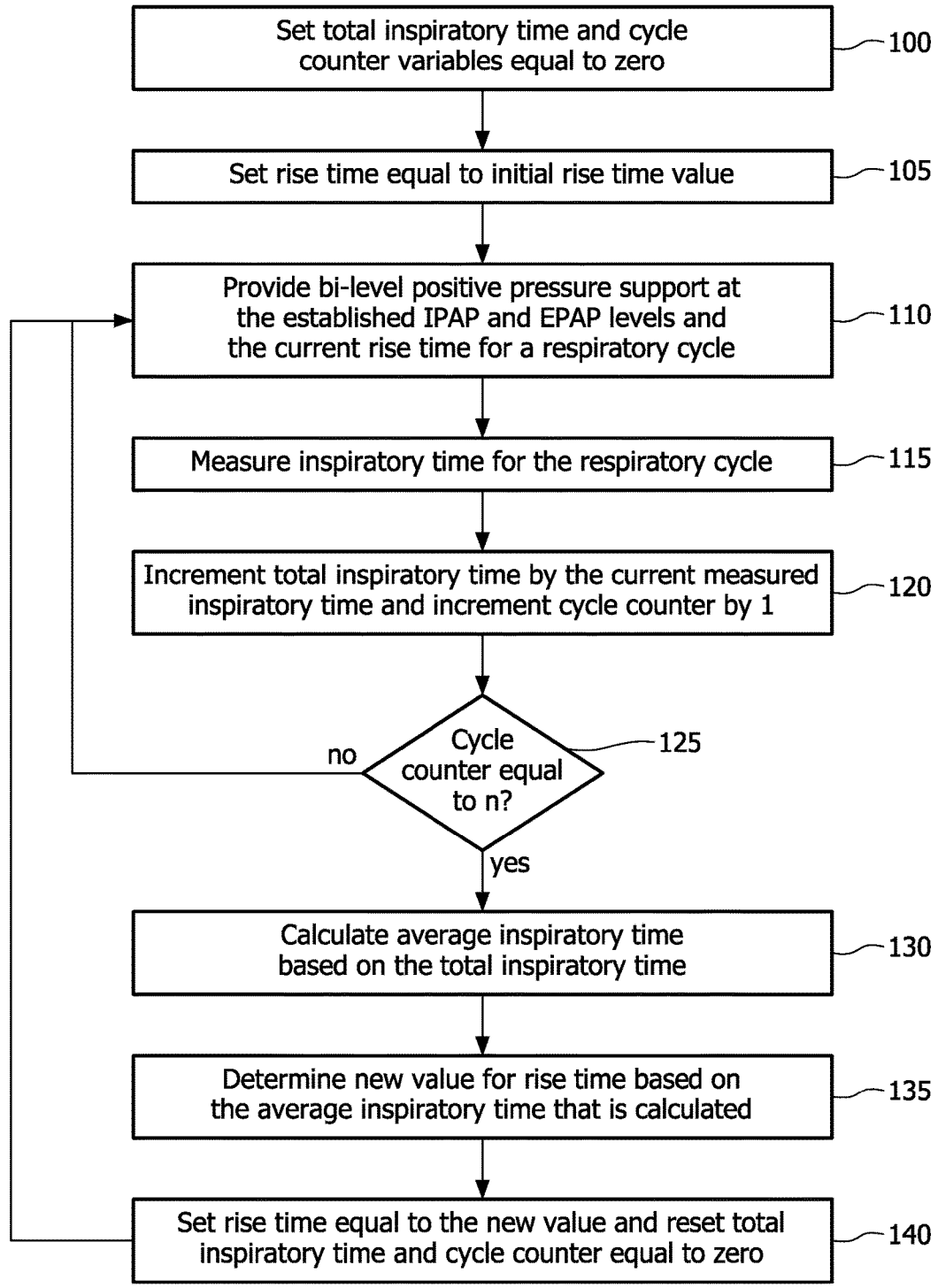
FIG. 4 is a flowchart showing a method of automatically adjusting rise time according to one particular, non-limiting embodiment of the invention.

FIG. 4 is a flowchart showing a method of automatically adjusting rise time according to one particular, non-limiting embodiment of the invention. As described in greater detail below, the method shown in FIG. 4 measures the average inspiratory time of the patient over N cycles and adjusts the rise time of the bi-level positive support therapy that is provided to the patient based on the determined average inspiratory time. Alternatively, rather than measuring the average inspiratory time of the patient over a set number of cycles, the average inspiratory time of the patient could be measured over a set time period (such as 30 seconds). In addition, the method shown in FIG. 4 employs a number of variables including a Total Inspiratory Time variable, which is used to accumulate time for the average inspiratory time calculations, a Cycle Counter variable, which is used to count respiratory cycles, and a Rise Time variable, which is used to control that rise time of the bi-level positive pressure support that is provided to the patient. Also, established IPAP and EPAP levels are set by a clinician (or the patient) for the therapy that is to be provided, for example by inputting values therefore into the pressure support system 50 using the input/output device 66.

Referring to FIG. 4, the method begins at step 100, wherein the Total Inspiratory Time and Cycle Counter variables are initialized to a zero value. Next, at step 105, the Rise Time variable is set equal to an initial value that, in an exemplary embodiment, is set by a clinician (or the patient) by inputting a value into pressure support system 50 using input/output device 66. At step 110, bi-level positive pressure support is then provided to the patient by the pressure support system at the established IPAP and EPAP levels and the current Rise Time for a single respiratory cycle. At step 115, the inspiratory time for the respiratory cycle is measured. This may be done in any of a number of suitable known or hereafter developed ways. For example, inspiratory time may be determined based upon the pressure signal generated by the pressure sensor that is part of the patient interface 58 and flow signal $Q_{MEASURED}$ that is generated by flow sensor 62 using any of a number of well known techniques. Alternatively, inspiratory time may be determined based upon measured EMG signals from the respiratory muscles, measured exhaled CO2, temperature or humidity, or measured movement of the chest wall using inductive plethysmography.

Next, at step 120, the Total Inspiratory Time variable is incremented by an amount equal to the just measured inspiratory time, and the Cycle Counter variable is incremented by 1. At step 125, a determination is then made as to whether the Cycle Counter is equal to N, which is the number of respiratory cycles over which the average inspiratory time is to be calculated. If the answer is no, then the method returns to step 110 for continued bi-level positive pressure therapy at the current Rise Time. If, however, the answer at step 125 is yes, then, at step 130, the average inspiratory time is calculated based on the Total Inspiratory Time variable (i.e., the Total Inspiratory Time variable is divided by N to get the average).

Next, at step 135, a new value for the Rise Time variable is determined based on the calculated average inspiratory time. This may be done in a number of ways. In one embodiment, the calculated average inspiratory time is multiplied by a predetermined constant to obtain the new value for the Rise Time (i.e., Rise Time=K*average inspiratory time). For example, a typical range for the inspiratory time is 0.5 seconds to 3 second at the extremes with 1-2 seconds being more typical. A "comfortable" Rise Time for an average inspiratory time of 1 second might be 0.2 seconds, and thus the constant K in this embodiment would be 0.2 sec/1 sec or 0.2. Note that the constant K is unitless. If average inspiratory time increased to 1.5 seconds, then, according to this embodiment, the new value for Rise Time would be 0.2*1.5 seconds or 0.3 seconds. Similarly, if average inspiratory time contracts to 0.5 seconds, then, according to this embodiment, the new value for Rise Time would be 0.2*0.5 seconds or 0.1 seconds. In this embodiment, the new value for Rise Time is further constrained to only be within certain predetermined safe high and low limits. Thus, if a calculated value new value exceeds the limits (high or low), it will in this embodiment be set equal to the limit value.

In the embodiment just described, the delivered pressure profile, Pp(t), is completely described by the rise time, IPAP and EPAP and may be given by $Pp(t)=(1-e^{-\alpha t/Trt}) \cdot (IPAP-EPAP)+EPAP$. The value of $\alpha$ adjusts the behavior such that rise time (Trt) can be defined as the time it takes to reach a defined percentage of IPAP−EPAP. If $\alpha$ is set to 1, then the first term of Pp(t) in this example reaches 63.2% of IPAP−EPAP at t=Trt. This is an advantageous method due to its simplicity and industry acceptance. However, other functions could be used to compute Pp(t) from rise time. For example, the first quarter cycle of a sine wave could work as represented by $Pp(t)=(IPAP-EPAP)\sin(2\pi\alpha t/Trt)+EPAP$, where $\alpha=\frac{1}{4}$ for Pp(Trt)=IPAP or $\alpha=0.117$ for Pp(t)=0.67* (IPAP−EPAP)+EPAP. Alternatively, a combination method could include $Pp(t)=(1-e^{-\alpha t/Trt})\cdot(IPAP-EPAP)+EPAP$ for Tinsp<1.5 seconds, and $Pp(t)=(IPAP-EPAP)\sin(2\pi t/Trt)+EPAP$ otherwise.

In an alternative embodiment, a look-up table can be established and stored by the pressure support system 50 that maps each of a plurality of average inspiratory time values (or ranges of such values) to a corresponding value for Rise Time. In this embodiment, step 135 would thus comprise consulting the look-up table to determine the value for Rise Time that corresponds to the average inspiratory time that is calculated in step 130. In still a further embodiment, a look-up table can be established and stored by the pressure support system 50 that maps each of a plurality of average inspiratory time values (or ranges of such values) to a corresponding first value that, when multiplied by a constant K will give a value for Rise Time. In this embodiment, step 135 would thus comprise consulting the look-up table to determine the first value that corresponds to the average inspiratory time that is calculated in step 130, and then multiplying the obtained first value by the constant to obtain the new value for Rise Time.

Following step 135, however implemented, the method proceeds to step 140, wherein the Rise Time variable is set equal to the new value that is determined in step 135. Also, the Total Inspiratory Time and Cycle Counter variables are reset to zero in step 140. Following step 140, the method returns to step 110, wherein bi-level positive pressure support therapy is provided to the patient at the new (current) Rise Time.

Figures 8A, 8B, 8C:
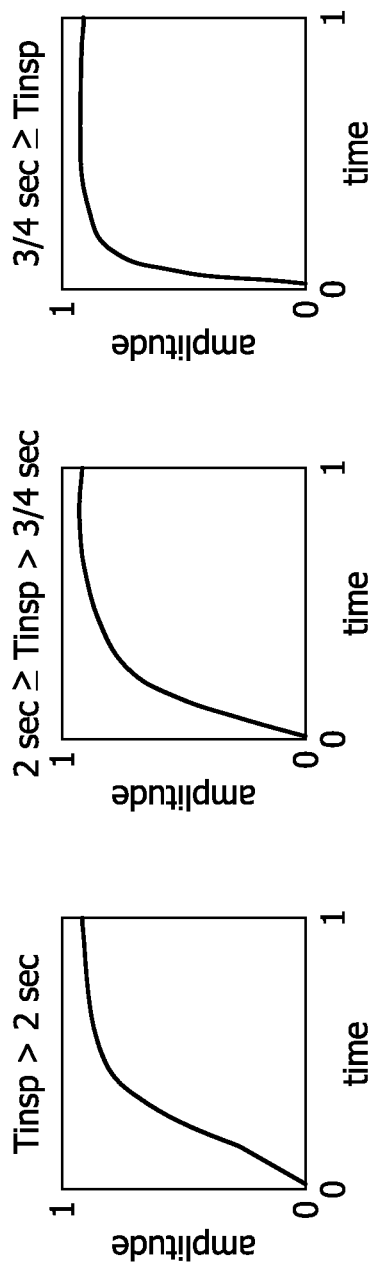
FIGS. 8A, 8B, and 8C illustrate using determined average inspiratory time to select one of several stored pressure profiles according to one particular embodiment.

Furthermore, the determined average inspiratory time could be used to select one of several pressure profiles stored in tables illustrated by the graphs shown in FIGS. 8A, 8B and 8C. The time and amplitude can be adjusted to match the required IPAP-EPAP and Trt using linear interpolation or any other methods well known in signal processing.

Sometimes the inspiratory time of a patient remains relatively constant (for example varying only +/−20%), while the total breath time (which is the duration of the entire respiratory cycle and includes inspiratory time and expiratory time) can be much more variable. For example, a typical total breath time can range from 1.5 seconds to 6 seconds. For a given inspiratory time, the patient may prefer a shorter rise time as the total breath time decreases. The clinical thinking here is that slow breathing (say less than 15 BPM or a total breath time greater than 4 second) does not need a fast rise time but the patient would likely appreciate a shorter rise time for faster paced breathing (e.g., greater then 20 BPM or total breath time less than three 3 second). Thus, in some circumstances, it may be desirable to automatically adjust rise time in bi-level positive pressure support therapy based not only on inspiratory time, but also based on total breath time.

Figure 5:
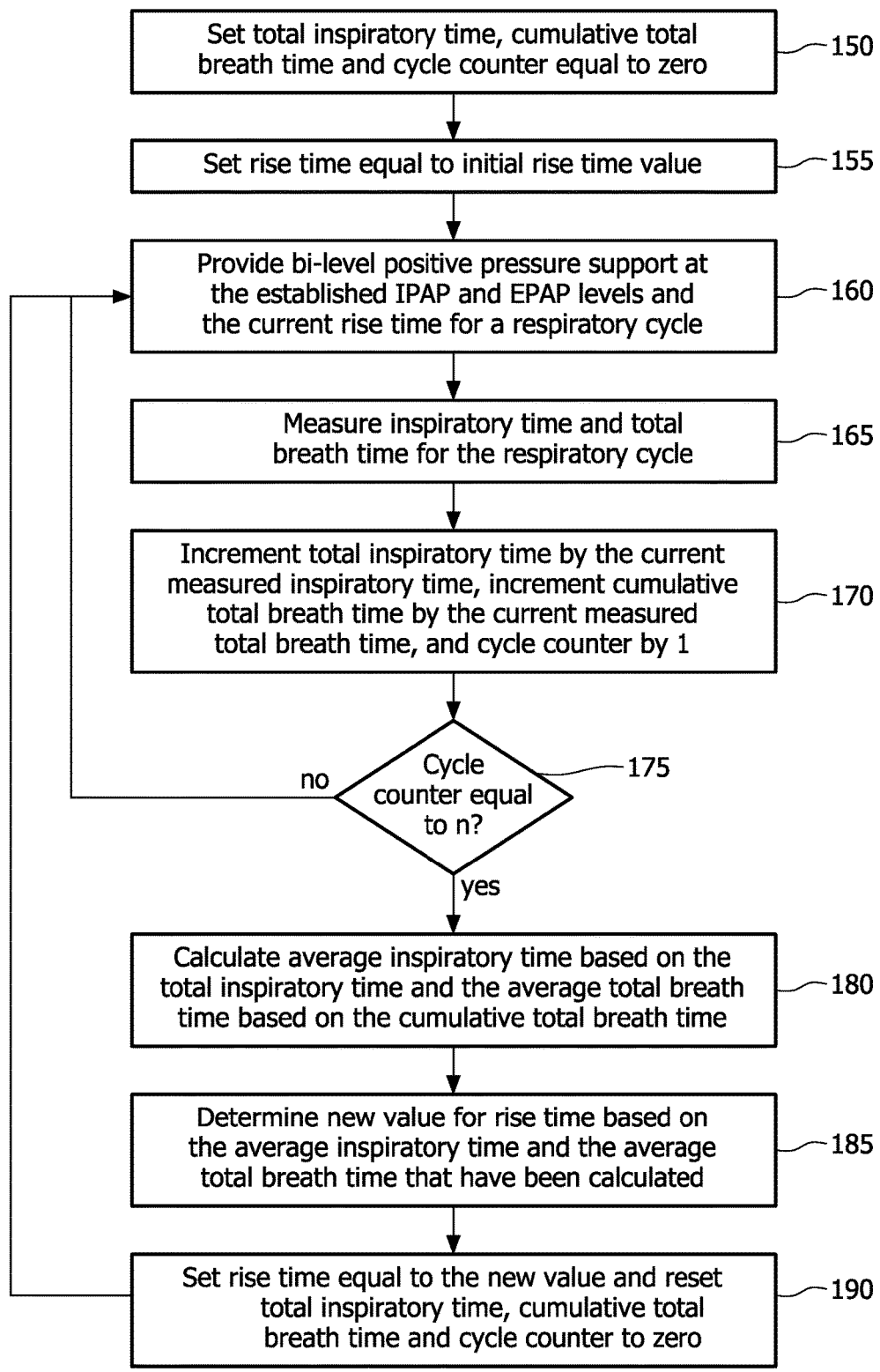
FIG. 5 is a flowchart showing a method of automatically adjusting rise time according to an alternative particular, non-limiting embodiment of the invention.

FIG. 5 is a flowchart showing a method of automatically adjusting rise time according to another particular, non-limiting embodiment of the invention wherein the rise time adjustment is based on both inspiratory time and total breath time. As described in greater detail below, the method shown in FIG. 5 measures the average inspiratory time and the average total breath time of the patient over N cycles and adjusts the rise time of the bi-level positive support therapy that is provided to the patient based on (i.e., as a function of) the determined average inspiratory time and the determined average total breath time. Alternatively, rather than measuring the average inspiratory time and the average total breath time of the patient over a set number of cycles, the average inspiratory time of the patient could be measured over a set time period (such as 60 seconds). In addition, like the method shown in FIG. 4, the method shown in FIG. 5 employs a number of variables including the Total Inspiratory Time variable, the Cycle Counter variable, and the Rise Time variable described elsewhere herein. In addition, the method of FIG. 5 also employs a Cumulative Total Breath Time variable, which is used to accumulate time for the average total breath time calculations. Also, as described elsewhere herein, established IPAP and EPAP levels are employed.

Referring to FIG. 5, the method begins at step 150, wherein the Total Inspiratory Time, Cumulative Total Breath Time and Cycle Counter variables are initialized to a zero value. Next, at step 155, the Rise Time variable is set equal to an initial value that is set by a clinician (or the patient) by inputting a value into pressure support system 50 using input/output device 66. At step 160, bi-level positive pressure support is then provided to the patient by the pressure support system at the established IPAP and EPAP levels and the current Rise Time for a single respiratory cycle. At step 165, the inspiratory time and the total breath time for the respiratory cycle is measured. This may be done in any of a number of suitable known or hereafter developed ways. For example, inspiratory time and total breath time may be determined based upon the pressure signal generated by the pressure sensor that is part of patient interface 58 and flow signal $Q_{MEASURED}$ that is generated by flow sensor 62 using any of a number of well known techniques. Alternatively, inspiratory time and total breath time may be determined based upon measured EMG signals from the respiratory muscles, measured exhaled CO2, temperature or humidity, or measured movement of the chest wall using inductive plethysmography.

Next, at step 170, the Total Inspiratory Time variable is incremented by an amount equal to the just measured inspiratory time, the Cumulative Total Breath Time variable is incremented by an amount equal to the just measured total breath time, and the Cycle Counter variable is incremented by 1. At step 175, a determination is then made as to whether the Cycle Counter is equal to N, which is the number of respiratory cycles over which the average inspiratory time and the average total breath time are to be calculated. If the answer is no, then the method returns to step 160 for continued bi-level positive pressure therapy at the current Rise Time. If, however, the answer at step 175 is yes, then, at step 180, the average inspiratory time is calculated based on the Total Inspiratory Time variable (i.e., the Total Inspiratory Time variable is divided by N to get the average) and the average total breath time is calculated based on the Cumulative Total Breath Time variable (i.e., the Cumulative Total Breath Time variable is divided by N to get the average).

Next, at step 185, a new value for the Rise Time variable is determined based on the calculated average inspiratory time and the calculated average total breath time. This may be done in a number of ways. In a non-limiting embodiment, a look-up table is established and stored by the pressure support system 50 that maps average inspiratory time values and average total breath time values to a corresponding value for Rise Time. For example, such a table may provide a number of associated range pairs for average inspiratory time and average total breath time and map each associated range pair to a value for Rise Time. Thus, for any given pair of calculated average inspiratory time and average total breath time values, that pair of values can be fit into a particular associated range pair and then be mapped to a value for Rise Time. Thus, in this embodiment, step 185 would comprise consulting the look-up table to determine the value for Rise Time that corresponds to the average inspiratory time and average total breath time that are calculated in step 180.

Following step 185, however implemented, the method proceeds to step 190, wherein the Rise Time variable is set equal to the new value that is determined in step 185. Also, the Total Inspiratory Time, Cumulative Total Breath Time and Cycle Counter variables are reset to zero in step 190. Following step 190, the method returns to step 160, wherein bi-level positive pressure support therapy is provided to the patient at the new (current) Rise Time.

In the particular methods shown in FIGS. 4 and 5, the average values for certain patient respiration parameters (namely inspiratory time and total breath time) are calculated by using traditional "averaging" techniques (i.e., a true mean value). That is not, however meant to be limiting, as other "averaging" techniques may also be used. Thus, as used herein, the term "average" shall mean a value indicating a central tendency of a data set, including, without limitation, a mean, a median, a mode or another similar value determined as described herein. For example, as an alternative to the technique shown in FIGS. 4 and 5, the "averaging" of the inspiratory times and breath times may be performed using filtering to eliminate the effects of errant inspiratory times and breath times. Such filtering techniques may be useful because in real clinical applications, patients do certain things, such as cough, talk, burp, hiccup, and/or move, which often cause a number of breaths to be irregular. The use of such filtering techniques to remove these breaths from the breath statistics before computing the updated rise time as describe herein would thus be beneficial. The present invention contemplates that the selection/rejection criteria are imposed to remove breath statistics that may have been generated by cough, sneeze, hiccup, body movement or other external events not related to breathing. Thus, the current breath times should be tested against times that are physiologically reasonable. For example, this could be defined by the following criteria: (1) $Texp > Tinsp > 4*Texp$; (2) $3 \text{ seconds} > Tinsp > 0.5 \text{ seconds}$; and (3) $6 \text{ seconds} > Tbreath > 1 \text{ second}$, where Texp is expiratory time, Tinsp is inspiratory time, and Tbreath is total breath time. Also, statistical analysis may be employed to find "typical" breath values (for both inspiratory and total breath times) and therefore eliminate errant inspiratory times and breath times.

Also, a median filter for performing the filtering is advantageous in that data on the extremities is completely ignored. In addition, the "averaging" using a median or similar filter as just described may either be done using a block method where the average time is computed from N contiguous breaths as described in FIGS. 4 and 5, or by the so-called well known boxcar average, where the idea is that the average is computed after each breath. There is of course, a continuum from compute after each breath to compute after every L breaths where L=1 for the classic boxcar average to L=N for the average of contiguous blocks of N.

Figure 6:
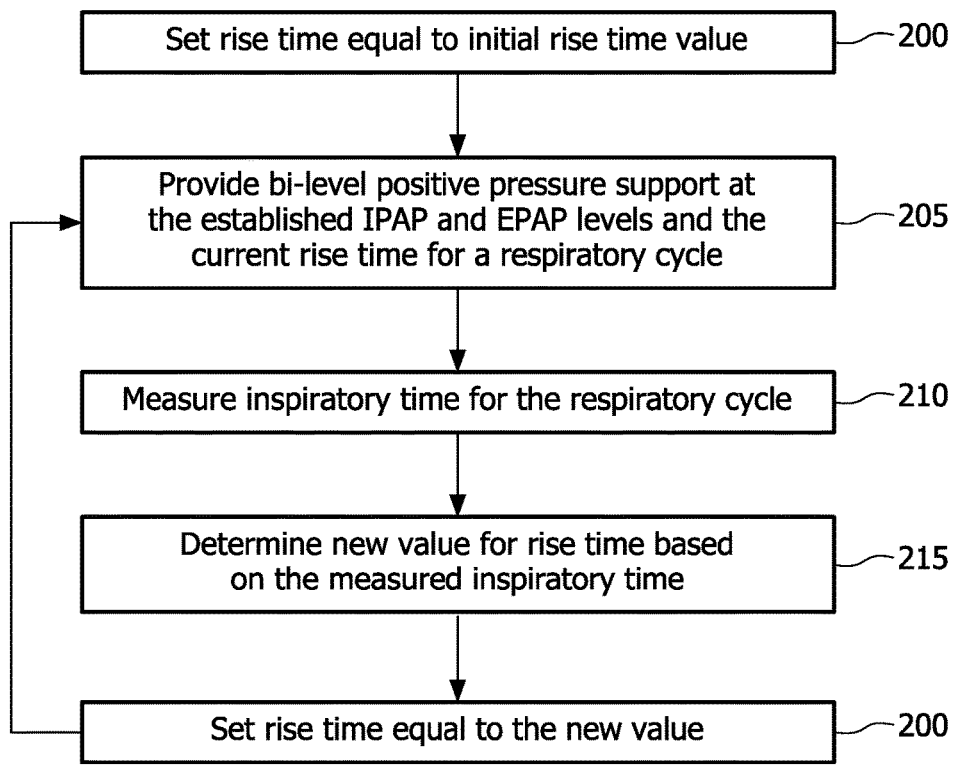
FIGS. 6 and 7 are flowcharts showing further alternative methods of automatically adjusting rise time.
Figure 7:
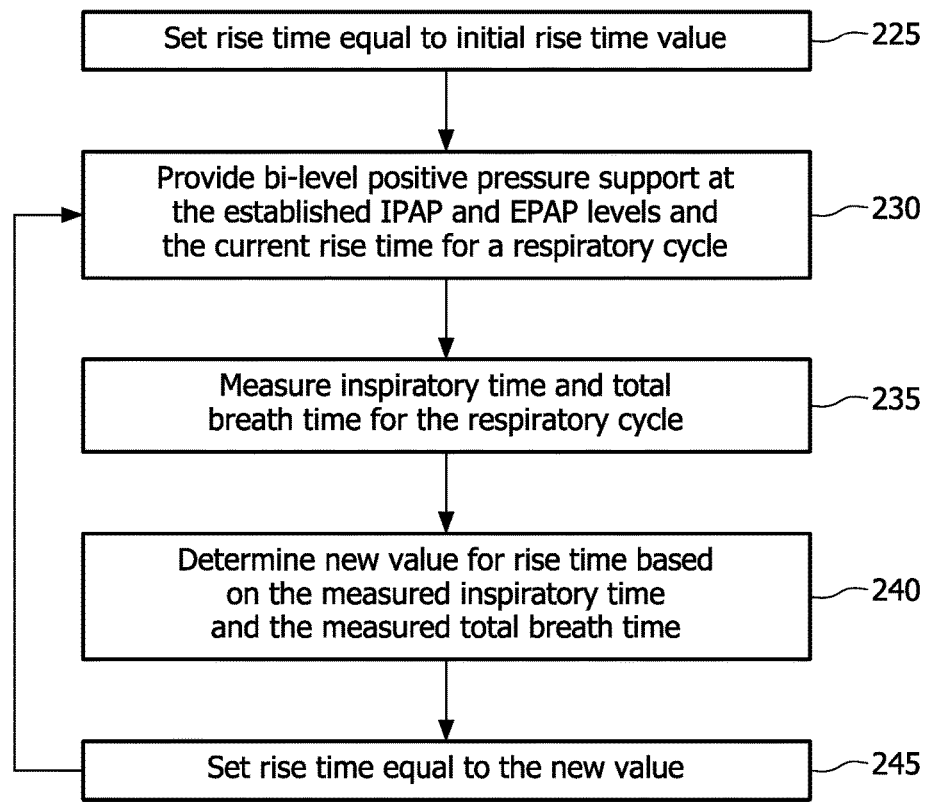

The methods of FIGS. 4 and 5 as described above automatically adjust rise time based on average values for certain patient respiration parameters (e.g., inspiratory time and total breath time). Thus, the rise time in those embodiments is adjusted periodically following a plurality of respiratory cycles. Alternatively, the rise time may be adjusted for each respiratory cycle based on a current value of a patient respiration parameter. FIGS. 6 and 7 are flowcharts of exemplary embodiments of methods that adjust rise time in this manner.

Referring to FIG. 6, in the method shown therein, inspiratory time is measured after each respiratory cycle and rise time is adjusted for the next cycle based on the measured value. The method begins at step 200, wherein the Rise Time variable is set equal to an initial value that is set by a clinician (or the patient) by inputting a value into pressure support system 50 using input/output device 66. At step 205, bi-level positive pressure support is then provided to the patient by the pressure support system at the established IPAP and EPAP levels and the current Rise Time for a single respiratory cycle. At step 210, the inspiratory time is measured. As described elsewhere herein, this may be done in any of a number of suitable known or hereafter developed ways. Next, at step 215, a new value for the Rise Time variable is determined based on the determined inspiratory time. As described elsewhere herein, this may be done in a number of ways (e.g., by multiplying by a constant or by consulting a look-up table). Following step 215, however implemented, the method proceeds to step 220, wherein the Rise Time variable is set equal to the new value that is determined in step 215. Following step 220, the method returns to step 205, wherein bi-level positive pressure support therapy is provided to the patient at the new (current) Rise Time.

Referring to FIG. 7, in the method shown therein, inspiratory time and total breath time are measured after each respiratory cycle and rise time is adjusted for the next cycle based on the measured values. The method begins at step 225, wherein the Rise Time variable is set equal to an initial value that is set by a clinician (or the patient) by inputting a value into the pressure support system 50 using the input/output device 66. At step 230, bi-level positive pressure support is then provided to the patient by the pressure support system 50 at the established IPAP and EPAP levels and the current Rise Time for a single respiratory cycle. At step 235, the inspiratory time and the total breath time are measured. As described elsewhere herein, this may be done in any of a number of suitable known or hereafter developed ways.

Next, at step 240, a new value for the Rise Time variable is determined based on the determined inspiratory time and the determined total breath time. This may be done in a number of different ways. In an exemplary, non-limiting embodiment, this is done by consulting a look-up table as described elsewhere herein. Following step 240, however implemented, the method proceeds to step 245, wherein the Rise Time variable is set equal to the new value that is determined in step 240. Following step 245, the method returns to step 230, wherein bi-level positive pressure support therapy is provided to the patient at the new (current) Rise Time.

Thus, as described in detail herein, the invention provides a number of different method embodiments that may be implemented in a suitable pressure support system that automatically adjust the rise time of bi-level positive pressure support therapy. By automatically adjusting the rise time of bi-level positive pressure support therapy, the costs associated with providing bi-level positive pressure support therapy in a home setting may be minimized as less home visits by a clinician or other provider are required.

Although the invention has been described in detail for the purpose of illustration based on what is currently considered to be the most practical and exemplary embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system, comprising:
a pressure generating system adapted to produce a flow of breathing gas;
a patient circuit operatively coupled to the pressure generating system to deliver the flow of breathing gas to an airway of a patient; and
a controller operatively coupled to the pressure generating system, the controller being adapted to determine an average inspiratory time of the patient while using the pressure support system and to control the pressure generating system to: (i) deliver the flow of breathing gas to the patient at an inspiratory positive airway pressure (IPAP) level during at least a portion of an inspiratory phase of the patient and deliver the flow of breathing gas to the patient at an expiratory positive airway pressure (EPAP) level that is less than the IPAP level during at least a portion of an expiratory phase of the patient, (ii) determine a rise time value as a function of the determined average inspiratory time, (iii) determine whether the rise time value is between a predetermined safe high limit and a predetermined safe low limit, (iv) automatically set a rise time associated with a transition from the EPAP level to the IPAP level to be equal to the rise time value if the rise time value is between the predetermined safe high limit and the predetermined safe low limit, and (v) automatically set the rise time associated with the transition from the EPAP level to the IPAP level to be equal to one of the predetermined safe high limit and the predetermined safe low limit if the rise time value exceeds the predetermined safe high limit or the predetermined safe low limit.

2. The pressure support system according to claim 1, further comprising a sensor operatively coupled to the controller, the sensor being adapted to measure a characteristic associated with the flow of breathing gas and to generate a signal indicative thereof, wherein the controller is adapted to receive the signal and to determine the average inspiratory time based thereon.

3. The pressure support system according to claim 2, wherein the sensor comprises a flow sensor and the signal comprises a flow signal, or wherein the sensor comprises a pressure sensor and the signal comprises a pressure signal.

4. The pressure support system according to claim 1, wherein the average inspiratory time of the patient is determined over (a) a predetermined number of respiratory cycles, or (b) a predetermined time period.

5. The pressure support system according to claim 1, wherein the rise time value is determined by (a) multiplying the average inspiratory time by a predetermined constant to determine the rise time value, or (b) consulting a stored look-up table using the average inspiratory time to determine the rise time value.

6. The pressure support system according to claim 1, wherein the controller is adapted to determine an average total breath time of the patient while using the pressure support system, and wherein the rise time value is determined as a function of both the determined average inspiratory time and the determined average total breath time.

7. The pressure support system according to claim 6, wherein the controller is adapted to determine the rise time value by consulting a stored look-up table using both the determined average inspiratory time and the determined average total breath time.

8. The pressure support system according to claim 1, wherein the transition from the EPAP level to the IPAP level is (a) an exponential ramp having a variable slope, or (b) a straight line ramp having a constant slope.

9. A method of providing pressure support to a patient, comprising: determining average an inspiratory time of the patient during therapy; delivering a flow of breathing gas to the patient at an inspiratory positive airway pressure (IPAP) level during at least a portion of an inspiratory phase of the patient; delivering the flow of breathing gas to the patient at an expiratory positive airway pressure (EPAP) level that is less than the IPAP level during at least a portion of an expiratory phase of the patient; determining a rise time value as a function of the determined average inspiratory time; determining whether the rise time value is between a predetermined safe high limit and a predetermined safe low limit; automatically setting a rise time associated with a transition from the EPAP level to the IPAP level to be equal to the rise time value if the rise time value is between the predetermined safe high limit and the predetermined safe low limit; and automatically setting the rise time associated with the transition from the EPAP level to the IPAP level to be equal to one of the predetermined safe high limit and the predetermined safe low limit if the rise time value exceeds the predetermined safe high limit or the predetermined safe low limit.

10. The method according to claim 9, wherein the average inspiratory time of the patient is determined over (a) a predetermined number of respiratory cycles, or (b) a predetermined time period.

11. The method according to claim 9, wherein the rise time value is determined by (a) multiplying the average inspiratory time by a predetermined constant to determine the rise time value, or (b) consulting a stored look-up table using the average inspiratory time to determine the rise time value.

12. The method according to claim 9, further comprising determining an average total breath time of the patient while using the pressure support system, wherein the rise time value is determined as a function of both the determined average inspiratory time and the determined average total breath time.

13. The method according to claim 12, wherein the rise time value is determined by consulting a stored look-up table using both the average inspiratory time and the average total breath time.

* * * * *